United States Patent

Eisenberg

[11] Patent Number: 5,080,097
[45] Date of Patent: Jan. 14, 1992

[54] COMBINATION PACER DEFIBRILLATOR ELECTRODES AND PACER-DEFIBRILLATOR AND METHOD FOR USE THEREWITH

[75] Inventor: Solomon R. Eisenberg, Newton, Mass.

[73] Assignee: Boston University, Boston, Mass.

[21] Appl. No.: 523,439

[22] Filed: May 14, 1990

[51] Int. Cl.$^5$ .............................................. A61N 1/04
[52] U.S. Cl. ................................ 128/419; 128/419.1; 128/783
[58] Field of Search ............... 128/419 D, 419 P, 783, 128/800

[56] References Cited

U.S. PATENT DOCUMENTS

| Re. 30,750 | 9/1981 | Diack et al. | 128/419 |
|---|---|---|---|
| 4,088,138 | 5/1978 | Diack et al. | 128/419 |
| 4,291,707 | 9/1981 | Heilman et al. | 128/419 D |
| 4,355,642 | 10/1982 | Alferness | 128/642 |
| 4,735,206 | 4/1988 | Hewson | 128/419 |
| 4,955,381 | 9/1990 | Way et al. | 128/419 D |

OTHER PUBLICATIONS

C. A. Williams, L. A. Geddes, J. D. Bourland and E. S. Furgason, "Analysis of the Current-Density Distribution from a Tapered, Gelled-pad External Cardiac Pacing Electrode," *Medical Instrumentation*, 21(6), Dec. 1987, pp. 329-334.

A. L. Aronson and B. Haggar, "The Automatic External Defibrillator-pacemaker: Clinical Rationale and Engineering Design," *Medical Instrumentation*, 20(1), Jan.-Feb. 1986, pp. 27-35.

"Two Methods for Homogeneous Filed Defibrillation and Stimulation", R. H. Geuze, *Medical & Biological Engineering & Computing*, Jul. 1983, pp. 518-520.

Yongmin Kim, "Optimal Electrode Designs for Electrosurgery, DeFibrillation, and External Cardiac Pacing", IEEE Transactions on Biomedical Engineering, vol. BME-33, No. 9, Sep. 1986, pp. 845-853.

J. D. Wiley, et al., "Analysis and Control of the Current Distribution under Circular Dispersive Electrodes", IEEE Transactions on Biomedical Engineering, vol. BME-29, No. 5, May 1982, pp. 381-385.

*Primary Examiner*—William E. Kamm
*Attorney, Agent, or Firm*—Hamilton, Brook, Smith & Reynolds

[57] ABSTRACT

A single paddle is capable of delivering pacing and defibrillating electrical pulses to a patient. In one embodiment, the paddle has a region of high electrical conductivity coupled to a defibrillating electrode for delivering defibrillating pulses. The paddle also includes a region of low electrical conductivity coupled to a pacing electrode for delivery pacing pulses. In an alternative configuration, a region of high electrical conductivity is sandwiched between regions of low electrical conductivity. The regions are comprised of polymeric gel or gel-filled foam.

35 Claims, 6 Drawing Sheets

COMBINATION PACER DEFIBRILLATOR ELECTRODES AND PACER-DEFIBRILLATOR AND METHOD FOR USE THEREWITH

BACKGROUND OF THE INVENTION

A large number of patients suffering from cardiac arrest may benefit from the application of therapeutic electrical pulses such as pacing pulses and defibrillating pulses. Pacing pulses are applied to pace a patient's heartbeat, whereas defibrillating pulses are applied to halt fibrillation of the heart. The strength and duration of pacing pulses is quite different from the strength and duration of defibrillating pulses. Typically, defibrillating pulses apply a current of 20 to 50 amperes to the patient for a single duration of 10 to 40 milliseconds. Pacing pulses, in contrast, apply a much lower current (in the range of 40 to 140 milliamperes) as a series of pulses over a much longer duration. Current pacing-/defibrillation units require two separate and independent electrode pairs: one for defibrillation and one for pacing.

SUMMARY OF THE INVENTION

The present invention concerns a combined pacing and defibrillation paddle for applying therapeutic electrical pulses to a patient. The electrical pulses may be either pacing or defibrillating pulses. The paddle is comprised of a region of high electrical conductivity connected to a defibrillating electrode. This region is used to deliver the defibrillating pulses to the patient. The paddle also contains a region of low electrical conductivity connected to a pacing electrode. The low conductivity region is used to deliver the pacing pulses to the patient The pacing electrode is distinct from the defibrillating electrode The pacing pulses are applied through the pacing electrode to the region of low electrical conductivity. The regions and the electrodes are surrounded by an encasement.

The region of high electrical conductivity is preferably surrounded by the region of low electrical conductivity. In one preferred embodiment, the regions are comprised of concentric annular regions. The regions may be comprised of polymeric gel. The region of high electrical conductivity preferably has a resistance on the order of 10 ohms, whereas the region of low electrical conductivity preferably has a resistance on the order of $10^3$ ohms In accordance with one alternative embodiment of this invention, an additional or second region of low electrical conductivity is included on the paddle. This second region of low electrical conductivity is preferably surrounded by the region of high electrical conductivity. The surrounding region of high electrical conductivity is, in turn, surrounded by the first region of low electrical conductivity.

These type of paddles are designed to be used in tandem with an additional paddle to form a paddle pair. The additional paddle is a receiving paddle for completing the circuit through the patient so that the pulses will flow through the patient from the delivery paddle to the receiving paddle. The delivery and receiving paddles may be of identical construction They are designed to be coupled to a pacing/defibrillation unit. The pacing-/defibrillation unit includes a pulse source for applying voltages to the delivery paddles. Thus, the invention provides a method of delivering both defibrillating pulses and pacing pulses using a plurality of paddles, at least one paddle having a region of high electrical conductivity and a region of low electrical conductivity, comprising the steps of a) generating defibrillating pulses by applying a voltage to the high conductivity region, and b) generating pacing pulses by applying a voltage to the low conductivity region.

DETAILED DESCRIPTION OF THE PREFERRED EMBODIMENT

In accordance with a preferred embodiment of the present invention, a delivery paddle is capable of delivering either electrical pacing pulses or electrical defibrillating pulses to a patient. The paddle is configured to meet the greatly differing electrical requirements of these different types of pulses in a single paddle package. This new paddle performs both the pacing and defibrillation functions as well as paddles currently available.

Figure 1A:
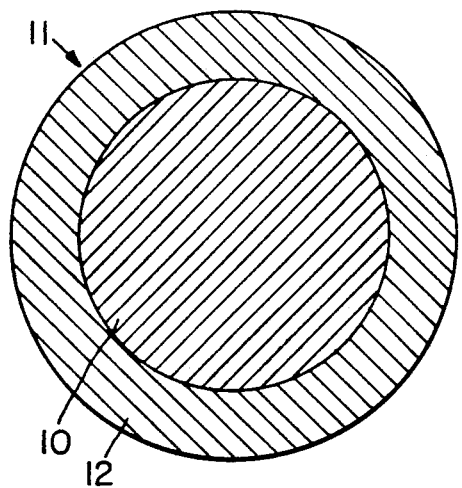
FIGS. 1a and 1b depict a first embodiment of the defibrillating/pacing paddle of the present invention.

The delivery paddle 11 of a first embodiment of the present invention (depicted in FIG. 1a) is comprised of two regions of different electrical conductivities (and thus, different electrical resistances). Specifically, an inner region 10 having a diameter of approximately 6–8 centimeters is comprised of polymeric gel or gel-filled foam and has a low electrical resistance on the order of 10 ohms. The foam or gel holds a substance such as sodium chloride that readily ionizes. This inner region 10 has a width of a few centimeters and is surrounded by a ring-like section 12 of high electrical resistance that is also comprised of polymeric gel or gel-filled foam which also holds a substance such as sodium chloride. The two regions 10 and 12 have approximately the same surface area. The primary distinction between the two regions lies in their different electrical resistances. The electrical resistance of the outer region 12 is on the order of $10^3$ ohms as opposed to on the order of 10 ohms resistance of the inner region. The difference in resistances is the result of different sodium chloride concentrations in the respective gel regions 10 and 12.

The gel or gel-filled foams employed in the inner region 10 and outer region 12 have a thickness of about 0.5 centimeters (as do most conventional gel based paddles). The paddle 11 is placed on the patient during the operation of the system; the gel at the surface of regions 10 and 12, thus, contacts the patient and acts as a conductant to assist in the application of the pacing or defibrillating pulse to the patient. Attached to the regions of gel 10 and 12 are annular shaped metal contacts 14 and 16 that act like electrodes. These metal contacts 14 and 16 are made of a suitable material such as stainless steel. Annular metal contact 14 is attached to the outer ring of gel or gel-filled foam 12. A lead wire 2 connected on the other side of the metal contact 14 carries the pulse from a voltage source (not shown) to the contact 14. The metal contact 16, on the other hand, is coupled to the inner region of gel or gel-filled foam 10 and receives the defibrillating pulses from a voltage source over a wire 2 that connects the voltage source to the metal contact 16.

Figure 1B:
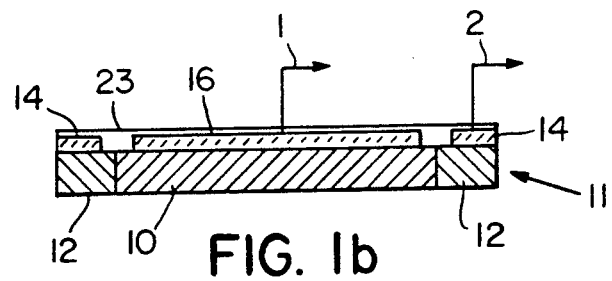

In one variation of this embodiment, the gel regions 10 and 12 as well as the metal contacts 14 and 16 are surrounded by an encasement 23 (Figure 1b). The encasement 23 may be made of any suitable material such as semi-rigid polyvinyl chloride (PVC) or polyethelene that serves to hold the components of the paddle 11 together in a single package. It should be noted that this variation is designed for applications that do not require physical separation of the adjacent gel regions 10 and 12. The design of paddle 11 purposely avoids such separation to enhance electrical interaction between regions 10 and 12. Another variation embodied within the present invention is to put a separate encasement around each region 10 and 12 so as to separate the regions. Such an encasement, however, would preferably not separate the gel regions entirely. The regions would be allowed to contact near the patient. This approach allows the paddle 11 to remain in storage for an extended period of time without fear of diffusion between the gel regions 10 and 12

Figure 7:
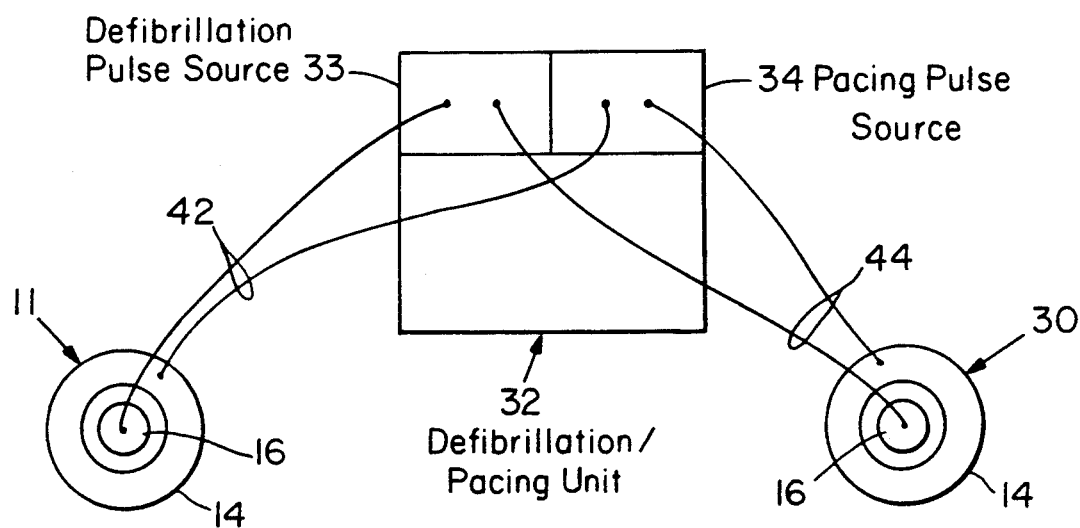
FIG. 7 illustrates a defibrillation/pacing unit with a delivery paddle and a receiving paddle.

The delivery paddle 11 is designed to be coupled to a defibrillation/pacing unit 32, as shown in FIG. 7. Connectors 42, 44 electrically couple the paddles 11, 30 to the defibrillation/pacing unit 32 which serves as a pulse source. The defibrillation/pacing unit 32 includes a defibrillation pulse source 33 and a pacing pulse source 34. The operator of the unit 32 selects the appropriate type of pulse: pacing or defibrillating. The operator then places the delivery paddle 11 in contact with the patient. A receiving paddle 30, (which is described below) is also placed in contact with the patient to complete the circuit through the patient. Once the delivery and receiving paddles are appropriately positioned, the electrical pulses are applied. The section of the paddle not being used (i.e. pacing or defibrillation) remains as an open circuit when the other portion of the paddle is in use. When the treatment is completed, the paddles are removed and discarded.

Placing the region 10 inside a region 12 of low conductivity helps to ease an edge effect that often occurs with defibrillation paddles. The edge effect is characterized by a large amount of current being concentrated on the outer edge of the paddle 11. Since the outer edge of the paddle is interfaced with a region of air and air has negligible conductivity, current can not generally pass out of the paddle into the surrounding air. Since the current does not crossover into the air, it remains concentrated on the outer edge. In the present invention, however, a region of low conductivity 12 surrounds the defibrillating region 10. Although the region of low conductivity is not an excellent conductor, it, nevertheless, still conducts. As a result, some of the current that would otherwise accumulate on the outer edge of region 22 crosses over to the region of low conductivity and softens the edge effect.

Figure 2A:
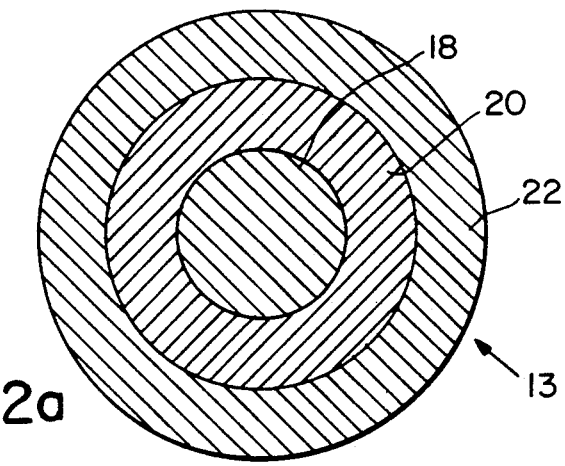
FIGS. 2a and 2b depict a second configuration of a defibrillating/pacing paddle of the present invention.
Figure 2B:
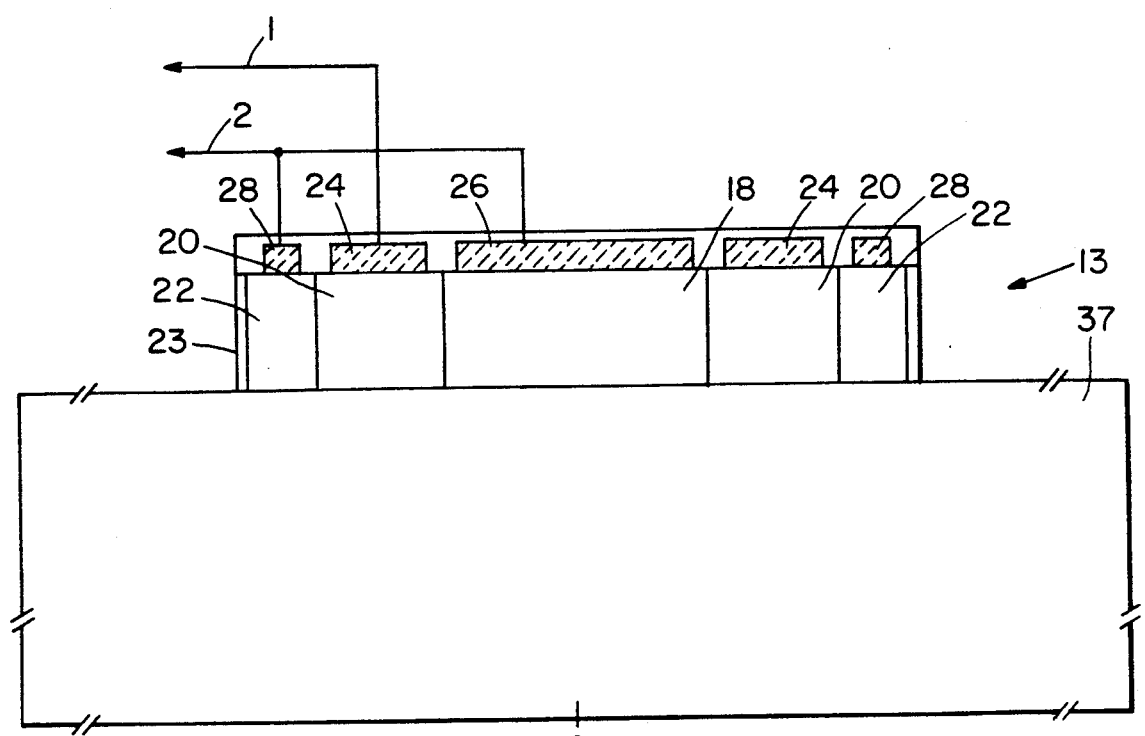

FIGS. 2a and 2b depict an alternative configuration that constitutes a second embodiment of the present invention. This paddle 13 is similar to the paddle 11 depicted in FIG. 1a except that it includes an additional concentric region of low electrical conductivity 18 at the center of the paddle 13. The electrical conductivity of the additional region 18 is 0.03 mS/cm (where S refers to Siemens which are defined as amperes per volt). This additional region of low electrical conductivity 18 has a radius of approximately 2.0 centimeters and is comprised of polymeric gel or gel-filled foam such as described with reference to the embodiment of FIG. 1a. The additional region 18 is surrounded by a ring 20 of high electrical conductivity that is, likewise, comprised of polymeric gel or gel-filled foam. The ring 20 has a conductivity of approximately 3.0 mS/cm. The inner radius of this ring 20 is at 2 cm and the outer radius is at 4 cm, relative to the center of the paddle 13. The region of high electrical conductivity 20 is, in turn, surrounded by an external ring 22 of low electrical conductivity. This outermost region 22 has a low conductivity of approximately 0.03 mS/cm. Its inner radius is at 4 cm, and its outer radius is at 5 cm. All of these regions 18, 20 and 22 are surrounded by an encasement 25 like that previously described with respect to paddle 11.

The region of low conductivity 22 aids in softening the edge effect such as region 12 does in the previously described paddle 11. Furthermore, the addition of region 18 in this second paddle 13 helps in applying pacing pulses. In particular, it provides additional area over which current may be spread to provide a uniform current density. Current density is an important concern because it is a primary determinant of patient comfort when pacing pulses are applied. Comfort to the patient during pacing pulses should be maximized because pacing typically is performed over an extended duration. The additional region 22, however, does not significantly affect the flow of current through region 20 when defibrillating pulses are applied because, due to the edge effect, little current flows through region 18.

The metal contacts 24, 26 and 28 of paddle 13 are organized in concentric fashion. Metal contacts 26 and 28, like those previously discussed, are made of a suitable material such as stainless steel and are attached to the regions 18 and 22 of low electrical conductivity. Metal contact 26 is positioned at the center of paddle 13 and has a radius of approximately 1.875 cm. Annular metal contact 24, in contrast, has an inner radius of 2.5 cm and an outer radius at 3.5 cm, relative to the center of the paddle 13. Lastly, annular metal contact 26 has an inner radius at 4.12 cm and an outer radius at 4.75 cm. Metal contacts 26 and 28 are coupled to regions 18 and 22 to deliver pacing pulses to those regions 18 and 22. Metal contact 24, however, is coupled to region 20, and delivers defibrillation pulses via region 20.

This delivery paddle 13 is designed, like the other alternative 11, to be used in tandem with a receiving paddle. The receiving paddle may be of identical design to the delivery paddle. The pulses are delivered via the delivery paddle 13 through the patient and received by the receiving paddle. This scheme provides a complete circuit so that current flows through the patient to produce the appropriate therapeutic effect.

The uniformity of current distribution in the approach adopted in FIG. 2a can be shown by examining plots of current densities for the paddle 13. For purpose of comparison, the paddle 13 may be compared with a conventional electrode with respect to plots of current densities. The conventional gel defibrillation electrode is modeled as 0.5 cm thick circular gel region with a radius of 5 cm and a conductivity of 3.0 mS/cm. The radius of the metallic contact on the surface of the conductive gel is 4.4 cm. The geometry used to model the pacing electrode is identical in every way to the defibrillation electrode. The sole difference between the pacing and defibrillation models is a gel having a conductivity of 0.03 mS/cm is used in the pacing model as opposed to a conductivity of 3.0 mS/cm in the defibrillating model. The electrodes rest on the surface of the body in the comparisions, which are modeled exactly as described previously. The body is modeled as a homogeneous cylindrical conductor 37 (see FIG. 2b) of radius 50 cm, a thickness of 25 cm and a conductivity of 3.0 mS/cm resting on a ground plane.

Figure 3:
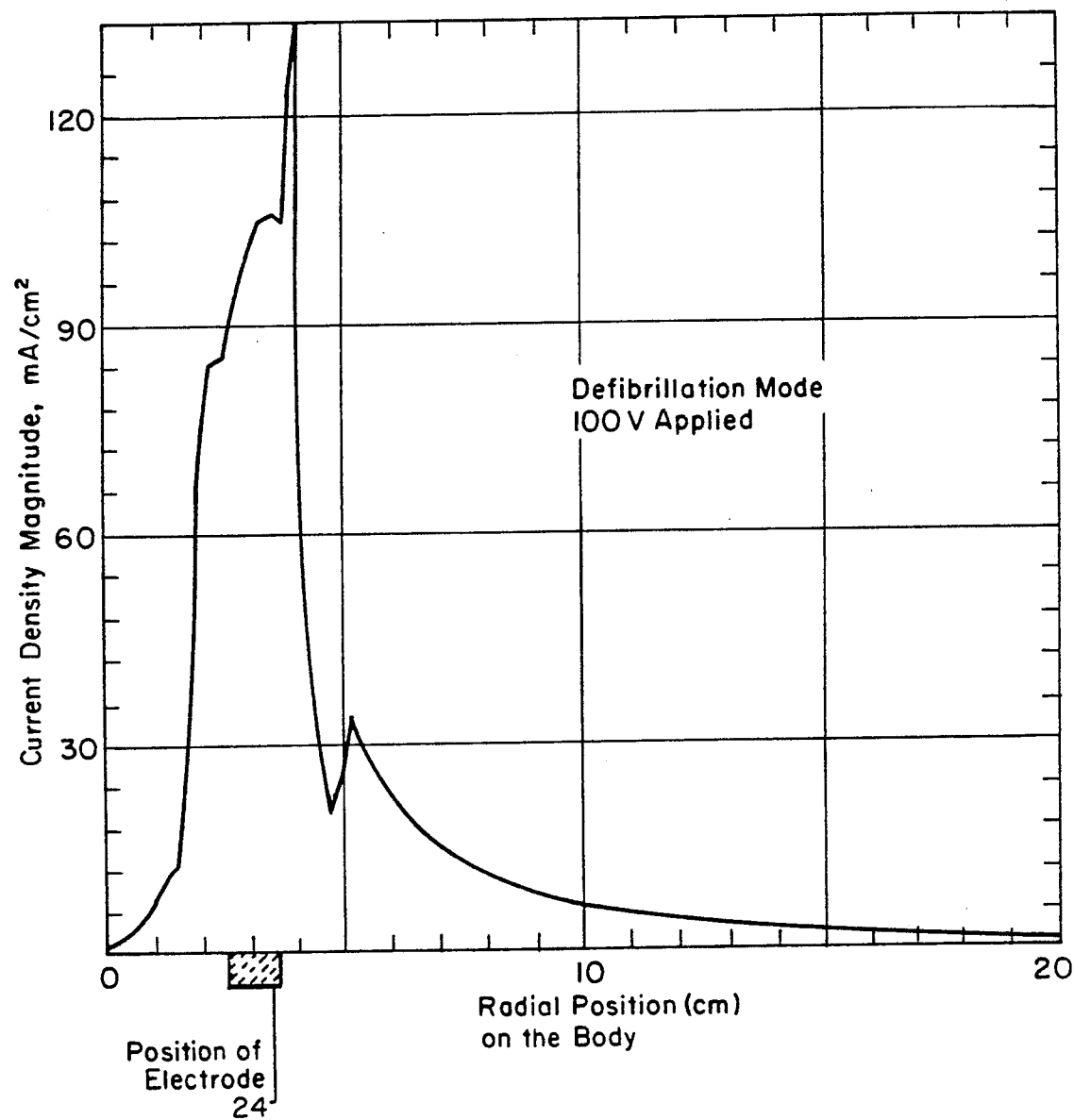
FIG. 3 depicts a plot of current density versus radial position for the second configuration of the paddle when defibrillation pulses are applied.
Figure 4:
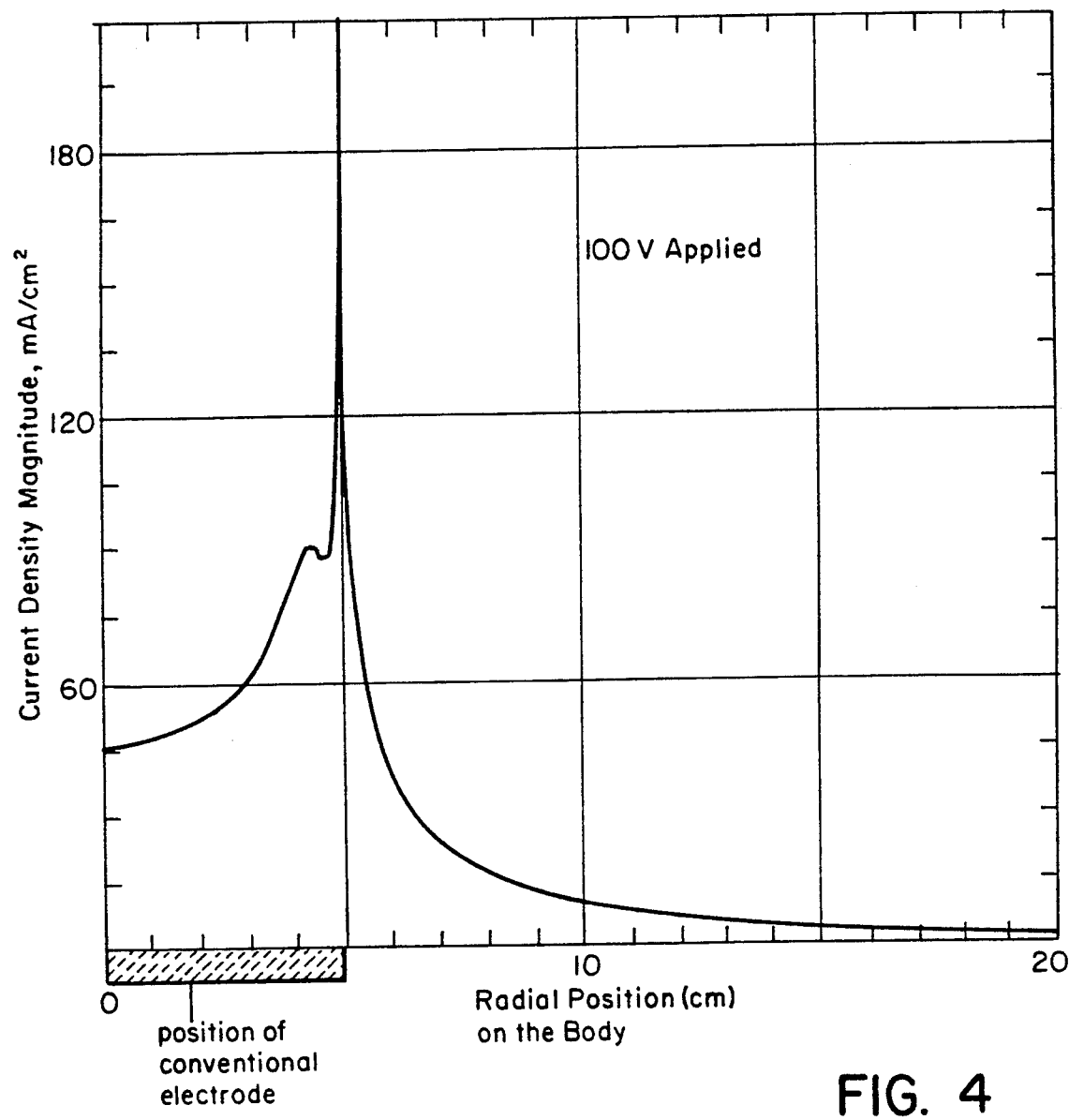
FIG. 4 shows a plot of current density versus radial position for a conventional defibrillation paddle.

FIG. 3 shows the magnitude of the current density at the surface of the skin produced by a 100 V defibrillation excitation applied to the middle annular metallic region 20 of the paddle 13 of FIG. 2a via electrode 24. For comparison, FIG. 4 shows the current distribution at the surface of the body that results from a 100 V excitation applied to the model of a conventional defibrillation electrode. It is evident that the paddle 13 of the present invention, when excited in the defibrillation mode, results in a peak current density magnitude at the body surface that is about 60% of the peak current magnitude in the corresponding conventional defibrillation electrode for the same voltage excitation. This results, in part, because the edge effect that dominates the distribution of current at the body surface with the conventional electrode is softened by the adjacent low but non-zero conductivity region 22 in the paddle 13. The reduction in current density magnitude also results because of the higher impedance of the paddle 13. The total impedance of the body and the paddle 13 is approximately 50% larger than the total impedance of the body and the conventional defibrillation electrode. The increase in impedance is due to the substitution of regions of low impedance such as in the conventional defibrillating electrode with regions of high impedance 18 and 22. The electrode can be made to deliver the same current by applying a proportionally larger voltage. Hence, if the respective electrodes in the paddle 13 are excited so as to deliver the same total current as the conventional paddle, the peak current density magnitudes for the two paddles will be comparable.

Figure 5:
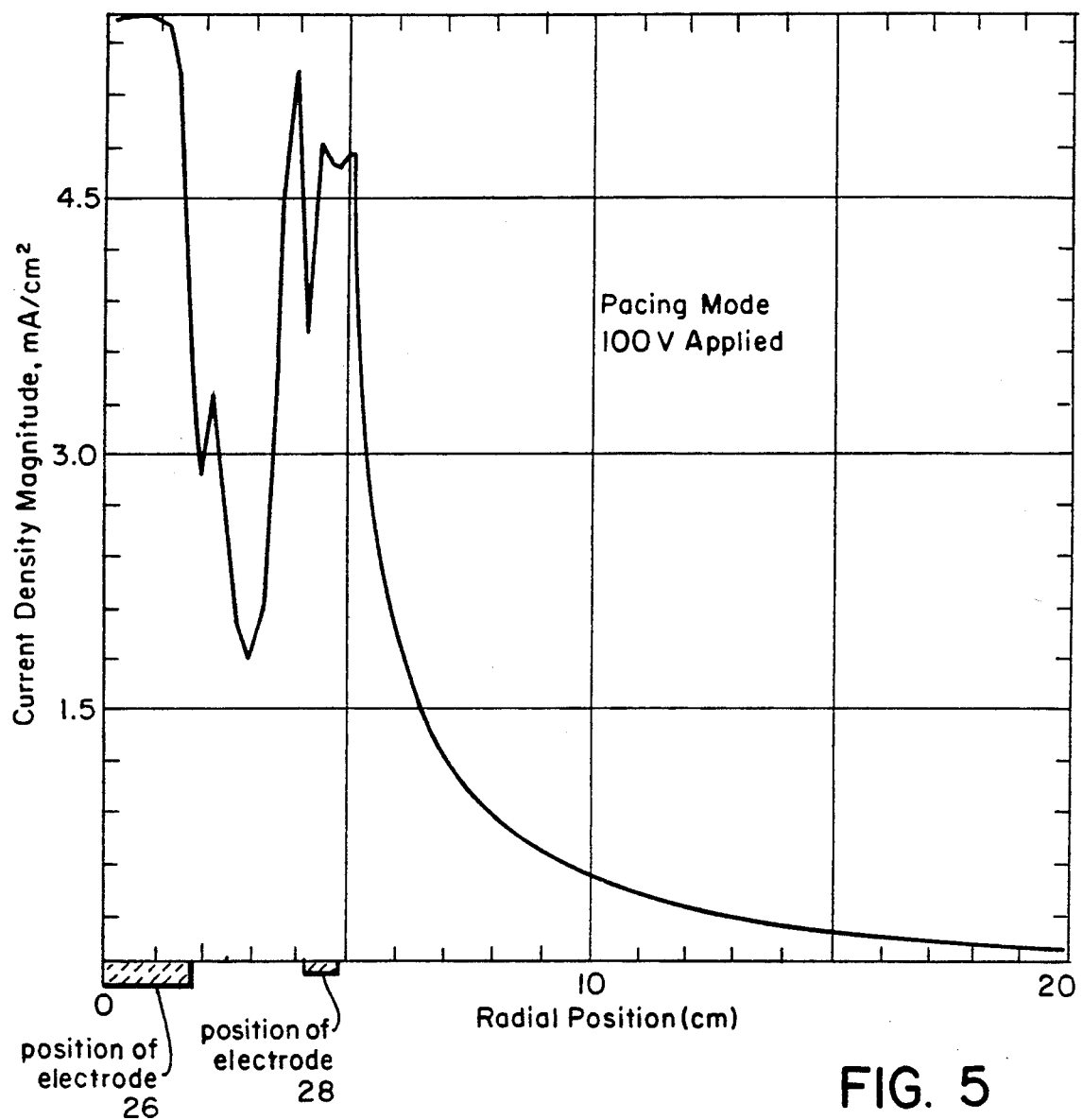
FIG. 5 illustrates a plot of current density versus radial position for the second configuration of the paddle when pacing pulses are applied.
Figure 6:
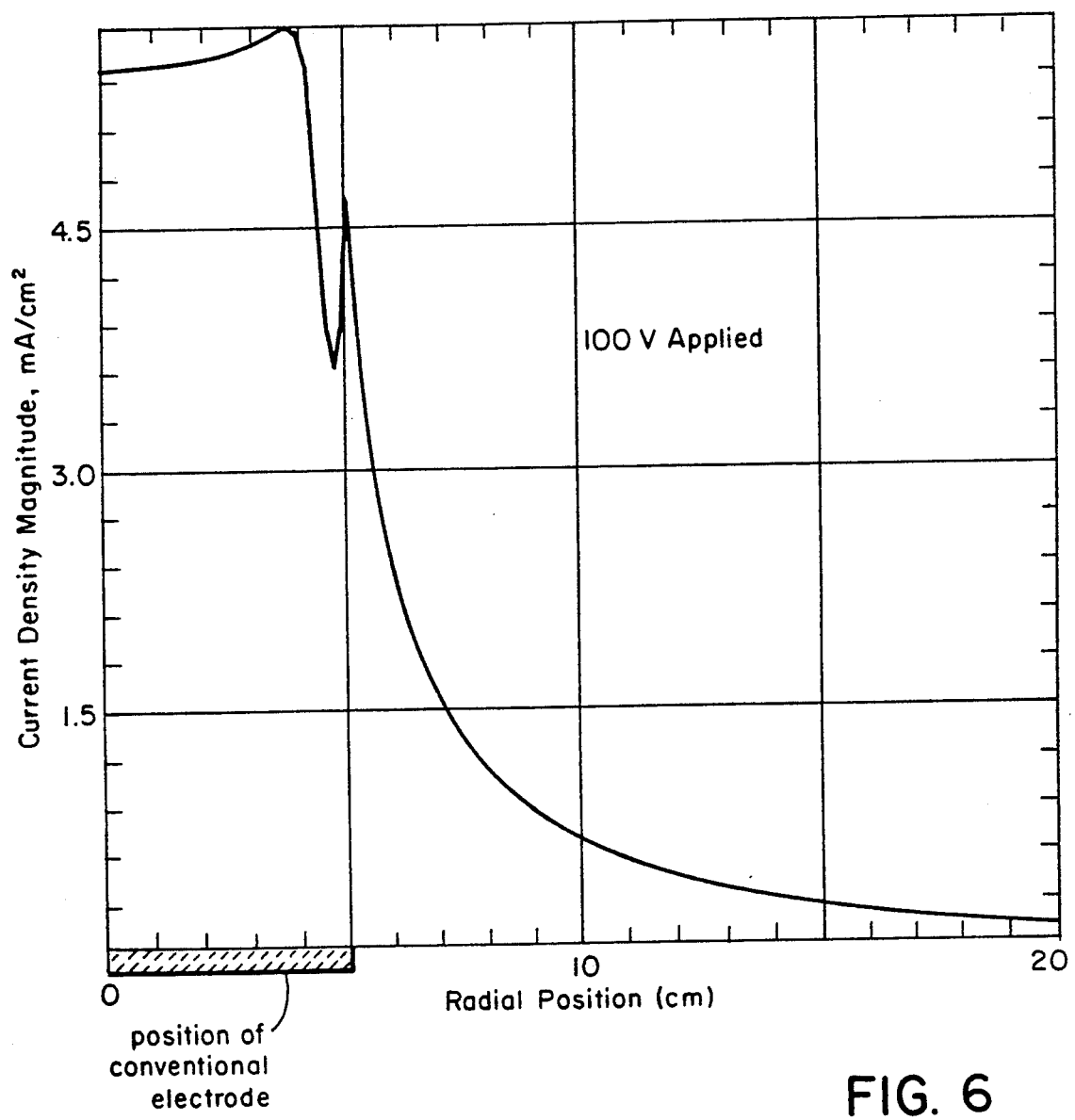
FIG. 6 depicts a plot of current density versus radial position for a conventional pacing paddle.

FIG. 5 shows the magnitude of the current density at the surface of the skin produced by a 100 V pacing excitation applied simultaneously to the central electrode 26 and the outer electrode 28 When excited in this mode, the electrodes 26 and 28 are intended to function as pacing electrodes. For comparison, FIG. 6 shows the current distribution at the surface of the body that results from a 100 V pacing excitation applied to the model of a conventional pacing electrode. It is evident that the paddle 13 when excited in the pacing mode results in a peak current density magnitude at the body surface that is essentially similar to the peak current magnitude in the corresponding conventional pacing electrode for the same voltage excitation. The distribution of current at the body surface is somewhat less uniform for the paddle 13 due to the absence of an excitation over the middle high conductivity annular region 20. The total impedance of the body and the paddle 13 when excited in the pacing mode is approximately 35% larger than the total impedance of the body and the conventional pacing electrode. The higher impedance is attributable to the smaller size of electrodes 26 and 28 relative to the conventional electrode. The addition of a region 20 of high conductivity does not offset the increase in impedance caused by the smaller electrodes 26 and 28 because region 20 is thin enough (i.e. 0.5 cm) to prevent much current from spilling over into it from the pacing regions 18 and 22. Hence, if the respective electrodes 26 and 28 are excited so as to deliver the same total current, the peak current density magnitudes for the paddle 13 will be approximately 35% larger than the corresponding conventional pacing electrode. Such a difference is not considered critical, and can be eliminated by a modest increase in the outer radius of the outer low conductivity region 22 and the corresponding electrode 28. As such, paddle 13 also performs as well as conventional electrodes when in the pacing mode.

The paddles 11 and 13 of both embodiments (i.e. of FIG. 1a and FIG. 2a) may be of different sizes to facilitate adult applications as well as for pediatric applications. The adult paddle has a diameter of around 10 cm, whereas the pediatric paddle has a diameter of about 2.5 inches. Moreover, the system is designed to be disposable. In particular, the paddles may be coupled with modular wiring so that they can be replaced as units merely by disconnecting the appropriate wiring.

While the invention has been particularly shown and described with reference to preferred embodiments thereof, it will be understood by those skilled in the art that various changes in form and details may be made without departing from the spirit and scope of the invention as defined in appended claims. For instance, the paddles may be configured in many different sizes and with many different gel configurations. Also different encasings and electrode configurations may be used. Still further, gels having different electrical conductivities may be used.

I claim:

1. A pacing and defibrillating paddle for placement in contact with a patient to apply pacing and defibrillating pulses to the patient, comprising:
   (a) a defibrillating electrode;
   (b) a region of high electrical conductivity connected to the defibrillating electrode, for delivering the defibrillating pulses, to the patient;
   (c) a pacing electrode; and
   (d) a region of low electrical conductivity connected to the pacing electrode that is distinct from the defibrillating electrode for delivering the pacing pulses to the patient, wherein the regions of conductivity are physically coupled.

2. A pacing and defibrillating paddle as recited in claim 1 wherein the regions are in electrical contact.

3. A pacing and defibrillating paddle as recited in claim 2 wherein the regions comprise concentric annular regions.

4. A pacing and defibrillating paddle as recited in claim 1 wherein the region of high electrical conductivity is encircled by the region of low electrical conductivity.

5. A pacing and defibrillating paddle as recited in claim 2 wherein the regions comprise concentric regions.

6. A pacing and defibrillating paddle as recited in claim 1 further comprising a second region of low electrical conductivity.

7. A pacing and defibrillating paddle as recited in claim 1 wherein the region of high electrical conductivity comprises a region of polymeric gel.

8. A pacing and defibrillating paddle as recited in claim 7 wherein the polymeric gel for the region of high electrical conductivity has an electrical resistance on the order of magnitude of 10 ohms.

9. A pacing and defibrillating paddle as recited in claim 1 wherein the region of low electrical conductivity comprises a region of polymeric gel.

10. A pacing and defibrillating paddle as recited in claim 9 wherein the polymeric gel for the region of low electrical conductivity has an electrical resistance on the order of magnitude of $10^3$ ohms.

11. A pacing and defibrillating paddle for placing in contact with a patient to deliver defibrillating pulses to the patient, comprising:
(a) at least one defibrillating electrode for delivering the defibrillating pulses to the patient;
(b) at least one pacing electrode for delivering the pacing pulses to the patient;
(c) a region of hydro-gel coupled to the defibrillating electrode, said hydro-gel having a high electrical conductivity; and
(d) a region of hydro-gel coupled to the said at least one pacing electrode, said hydro-gel having a low electrical conductivity, wherein the regions of conductivity are physically coupled.

12. A pacing and defibrillating paddle as recited in claim 1 wherein the regions of hydro-gel are in electrical contact.

13. A pacing and defibrillating paddle as recited in claim 11 further comprising an additional region of the hydro-gel coupled to the pacing electrode, said additional region having a low electrical conductivity.

14. A pacing and defibrillating paddle as recited in claim 13 wherein the regions comprise concentric regions.

15. A pacing and defibrillating paddle as recited in claim 11 further comprising an encasement for encasing the regions and electrodes.

16. A pacing and defibrillating paddle as recited in claim 11 wherein the region of low electrical conductivity has a resistance on the order of magnitude of $0^3$ ohms.

17. A pacing and defibrillating paddle as recited in claim 11 wherein the region of high electrical conductivity has a resistance on the order of magnitude of 10 ohms.

18. A pair of paddles for applying pacing and defibrillating pulses to a patient, comprising:
(a) a delivery paddle capable of delivering both the defibrillating and the pacing pulses to a patient, said delivery paddle being comprised of
 (1) a region of high electrical conductivity that is coupled to at least one defibrillating electrode for delivering the defibrillating pulses to the patient;
 (2) a region of low electrical conductivity that is coupled to at least one pacing electrode for delivering the defibrillating pulses to the patient wherein the regions of conductivity are physically coupled;
(b) a receiving paddle for receiving electrical pulses from the patient; and
(c) a pulse source, connected to said delivery and receiving paddles, for applying voltages to the delivery paddle to generate the defibrillating and the pacing pulses.

19. A pair of paddles as recited in claim 18 wherein the regions of the delivery paddle are in electrical contact.

20. A pair of paddles as recited in claim 18 wherein the receiving paddle has an identical construction to the delivery paddle.

21. A pair of paddles as recited in claim 18 wherein the delivery paddle further comprises an additional region of low electrical conductivity 22. A pair of paddles as recited in claim 21 wherein the regions comprise concentric regions.

23. A pair of paddles as recited in claim 22 wherein the additional region of low conductivity is surrounded by the region of high conductivity which, in turn, is surrounded by the region of low electrical conductivity.

24. A pair of paddles as recited in claim 22 wherein the region of high electrical conductivity is encircled by at least one region of low electrical conductivity.

25. A pair of paddles as recited in claim 18 wherein the region of high electrical conductivity has an electrical resistance on the order of magnitude of 10 ohms.

26. A pair of paddles as recited in claim 18 wherein the region of low electrical conductivity has an electrical resistance on the order of magnitude of $10^3$ ohms 27. A pair of paddles as recited in claim 18 wherein the regions are comprised of hydro-gel.

28. A pacing/defibrillation unit for applying pacing pulses or defibrillating pulses, comprising:
(a) a pulse source for applying voltages to a delivery paddle to generate the defibrillating and the pacing pulses;
(b) the delivery paddle for delivering the defibrillating and the pacing pulses to the patient, said delivery paddle being comprises of:
 (1) at least one pacing electrode;
 (2) at least one defibrillating electrode;
 (3) a region of high electrical conductivity coupled to the defibrillating electrode, said region being placed in contact with the patient to deliver the defibrillating pulses;
 (4) a region of low electrical conductivity coupled to the pacing electrode, said region being placed in contact with the patient to deliver the pacing pulses;
(c) a receiving paddle for receiving the defibrillating and the pacing pulses; and
(d) connectors for electrically connecting the electrodes to the pulse source.

29. A pacing/defibrillation unit as recited in claim 28 wherein the pulse source delivers different voltages to the pacing electrodes than to the defibrillating electrodes.

30. A pacing/defibrillation unit as recited in claim 28 wherein the receiving paddle has an identical construction to the delivery paddle.

31. A pacing/defibrillation unit as recited in claim 28 wherein the regions of the delivery paddle include concentric regions.

32. A pacing/defibrillation unit as recited in claim 28 wherein the region of high electrical conductivity is encircled by the region of low electrical conductivity.

33. A pacing/defibrillation unit as recited in claim 28 wherein the delivery paddle further comprises an additional region of low electrical conductivity.

34. A pacing/defibrillation unit as recited in claim 33 wherein the additional region of low electrical conductivity is surrounded by the region of high electrical conductivity which, in turn, is surrounded by the other region of low electrical conductivity.

35. A method of delivering both defibrillating pulses and pacing pulses using a plurality of paddles, at least one paddle having a region of high electrical conductivity and a region of low electrical conductivity, comprising the steps of:
 (a) generating defibrillating pulses by applying a voltage to the high conductivity region; and
 (b) generating pacing pulses by applying a voltage to the low conductivity region.

* * * * *